United States Patent [19]
Nozawa et al.

[11] Patent Number: 5,548,393
[45] Date of Patent: Aug. 20, 1996

[54] OIL DETERIORATION DETECTION APPARATUS AND APPARATUS FOR DETECTING PARTICLES IN LIQUID

[75] Inventors: Masaei Nozawa, Okazaki; Yasuyoshi Toda, Anjo; Kiwamu Naito, Kariya; Yurio Nomura, Nagoya; Rie Osaki, Anjo, all of Japan

[73] Assignee: Nippondenso Co., Ltd., Kariya, Japan

[21] Appl. No.: 269,587

[22] Filed: Jul. 1, 1994

[30] Foreign Application Priority Data

| Jul. 5, 1993 | [JP] | Japan | 5-192005 |
| Aug. 24, 1993 | [JP] | Japan | 5-209509 |
| Nov. 29, 1993 | [JP] | Japan | 5-326055 |

[51] Int. Cl.$^6$ .......................... G01N 21/15; G01N 33/30
[52] U.S. Cl. .................. 356/70; 340/631; 356/445; 359/507; 359/509
[58] Field of Search .................. 356/70, 445, 359; 359/507, 509; 340/607, 631, 619

[56] References Cited

U.S. PATENT DOCUMENTS

| 3,049,964 | 8/1962 | Miller et al. | 356/70 |
| 3,669,545 | 6/1972 | Gilby | 356/246 X |
| 3,902,807 | 9/1975 | Fleming et al. | 356/51 X |
| 3,939,457 | 2/1976 | Nelson | 340/607 |
| 4,447,546 | 5/1984 | Hirschfeld | 356/445 X |
| 4,602,869 | 7/1986 | Harrick | 356/246 X |
| 4,675,662 | 6/1987 | Kondo et al. | 340/631 |
| 4,699,509 | 10/1987 | Kamiya et al. | 356/70 |
| 5,049,742 | 9/1991 | Hosonuma et al. | 356/70 X |

FOREIGN PATENT DOCUMENTS

| 80632 | 6/1983 | European Pat. Off. . | |
| 426884 | 5/1991 | European Pat. Off. . | |
| 442314 | 8/1991 | European Pat. Off. . | |
| 57-142546 | 9/1982 | Japan | 356/70 |
| 61-164144 | 7/1986 | Japan | 356/70 |
| 62-193549 | 12/1987 | Japan . | |
| 63-266342 | 11/1988 | Japan . | |
| 3111741 | 5/1991 | Japan . | |
| 3142349 | 6/1991 | Japan . | |

Primary Examiner—Vincent P. McGraw
Attorney, Agent, or Firm—Cushman, Darby & Cushman

[57] ABSTRACT

An apparatus for detecting the concentration of particles in a liquid includes a light-emitting portion for emitting examination light which is totally reflected by a boundary surface contiguous to the liquid to be examined, a photosensor for receiving the totally-reflected light, a reference sensor for directly receiving the examination light, and a judgment portion for finding the reflectance from outputs of the two sensors to compute the particle concentration. In case that the liquid to be examined is lubricating oil of an engine, the concentration of carbon particles is calculated, thereby judging the deterioration of the lubricating oil.

10 Claims, 13 Drawing Sheets

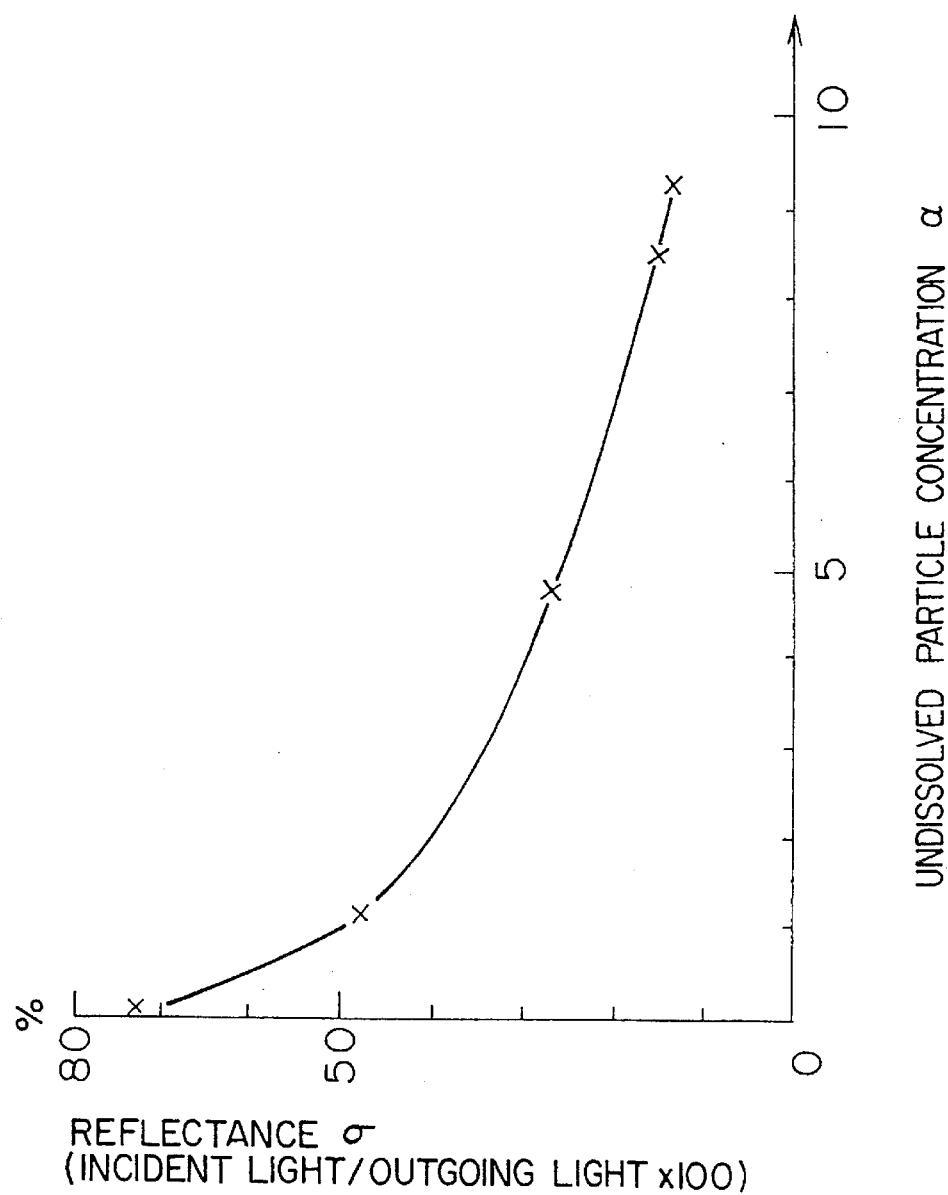

ial oil deterioration detection apparatus in which in view of the fact that the condition of carbon particles included in oil accurately reflects oil deterioration, the oil deterioration is detected by detecting the condition of carbon particles included in the oil.

A further object of this invention is to provide a practical oil deterioration detection apparatus in which the condition of carbon particles included in oil is detected by an optical method to thereby detect oil deterioration.

A still further object of the invention is to provide an oil deterioration detection apparatus in which oil deterioration is detected by an optical method, and the distance of transmission of light in oil can be accurately set to a predetermined length, and the lowering of a detection precision due to stains on a light-incident surface and a light-outgoing surface can be suppressed.

A further object of the invention is to provide an apparatus in which the size (diameter) of carbon particles included in oil can be detected with a relatively simple method.

A further object of the invention is to provide an apparatus for detecting particles in a liquid, in which the particles included in the liquid can be detected with a high precision.

A further object of the invention is to provide a particle detection apparatus in which particles included in a liquid can be detected using an optical method, and the distance of transmission of light in the liquid can be accurately set to a predetermined length, and besides the lowering of a detection precision due to stains on a light-incident surface and a light-outgoing surface can be suppressed.

A further object of the invention is to provide a particle detection apparatus in which particles included in a liquid can be detected using an optical method, and the lowering of a detection precision due to a change in the amount of light from a light-emitting portion can be suppressed.

A further object of the invention is to provide an oil deterioration detection apparatus, as well as an apparatus for detecting particles in a liquid, which can be easily installed.

To this end, according to the present invention, there is provided an apparatus for detecting the concentration of particles in a liquid (hereinafter often referred to as "particle concentration detection apparatus", which comprises a light-emitting portion, disposed in contact with the liquid (hereinafter referred to as "examination-undergoing liquid") to be examined, for emitting examination light to be totally reflected by a boundary surface thereof, a photosensor for receiving the totally reflected light, a reference photosensor for directly receiving the examination light, and a judgment portion for finding a reflectance from output signals from the two photosensors and for calculating the particle concentration of the liquid from this reflectance.

A first point to be most noted in the present invention is that the examination light emitted to the examination-undergoing liquid from the light-emitting portion is totally reflected by the boundary surface thereof.

Namely, if the refractive index of the examination-undergoing liquid is represented by $n_2$, and the refractive index of the light-emitting portion (hereinafter referred to as "boundary portion") forming a detection surface in contact with the examination-undergoing liquid is represented by $n_1$, the position of a light source and the refractive index $n_1$ of the boundary portion are so determined that the angle $\theta_1$ of incidence of the examination light is larger than the total reflection angle $\theta_c$ ($=\sin^{-1} n_2/n_1$).

A second point to be noted in the present invention is that the photosensor is provided at such a position as to receive the totally reflected light, and that there is provided a reference photosensor for directly receiving the examination light.

The judgment portion is an operation circuit which calculates the reflectance from the output signals of the two photosensors varying in accordance with the particle concentration, and judges the particle concentration of the examination-undergoing liquid from this reflectance.

The particle concentration detection apparatus may be used as a lubrication oil deterioration apparatus for a diesel engine, which judges the lubrication oil deterioration from the carbon particles concentration.

Preferably, there is provided a receiving portion for containing the examination-undergoing liquid, and cleaning members, which can be floated by movement of the examination-undergoing liquid, are included in the receiving portion.

The cleaning members are floated by the movement (including convection) of the examination-undergoing liquid to collide with the detection surface. The repetition of collision prevents foreign matters from depositing on the detection surface, so that the hindrance to the entering of the examination light, as well as a change in the amount of the light received by the photosensor, is suppressed.

Although there is a fear that the amount of the reflection light may be varied when such cleaning members are included in the liquid, such a disadvantage is eliminated by a method in which the time of measurement of the light is made longer than a certain time period, and the average value during that time period is used.

Namely, the cleaning members float, and therefore variations of the frequency of intrusion of the cleaning members into the path of the light to be reflected, if the measurement time is made longer than a predetermined time period, can be almost cancelled.

In a conventional particle concentration detection apparatus of the light-transmitting type, it is extremely difficult to include such cleaning members in a receiving portion.

One reason for this is that the distance between a light-incident portion and a light-outgoing portion is extremely small with a liquid of a low transmittance. A second reason is that as a result of inclusion of the cleaning members, the transmitting light is intercepted, so that the amount of the received light varies.

Preferably, there are provided a plurality of detection surfaces which are in contact with the examination-undergoing liquid, and cause the examination light to be totally reflected at their boundary surface, and there is formed such an optical path in which the examination light, emitted from the light source of the light-emitting portion, is totally reflected by the plurality of detection surfaces, and then reaches the photosensor.

By thus providing the plurality of detection surfaces, the rate of change of the totally reflected light with respect to the examination-undergoing liquid is greatly increased.

As described later in detail, the intensity of the totally reflected light at the detection surface varies (decreases) in accordance with the particle concentration of the examination-undergoing liquid. If the total reflection is effected a plurality of times at the plurality of detection surfaces, the rate of change of the totally reflected light is accumulated, and as a result the rate of change, which can not be easily detected by only one total reflection, can be increased into such a change rate as to be easily detected.

The optical path, by which the total reflection is effected at the plurality of detection surfaces as described above, can be formed by arranging the plurality of detection surfaces at different angles, respectively, or by suitably providing mirrors or the like for changing the direction of the examination light.

Preferably, a plurality of mirrors or the like are provided in the optical path leading from the light source to the photosensor, thereby changing the direction of the optical path in such a manner that the total reflection light can be incident on the photosensor mounted on a board having the light source mounted thereon.

If the light source and the photosensor are thus mounted on the common board, the two members can be easily mounted during the assembling process since they are to be mounted on the common board, and only one board is needed, so that the cost can be reduced.

Ordinary circuit components to be mounted on a board can be mounted on a common board since no limitation of an optical mounting angle is imposed on these components. On the other hand, the mounting angle of the light source and the photosensor is limited because of optical requirements, and the two are usually required to be mounted on different boards, respectively. Therefore, the two have been mounted on different boards, respectively, or have been mounted outside of the board having the circuit components mounted thereon. However, with the above arrangement, the above problem is overcome, thus enabling the two members to be mounted on a common board.

More specifically, rays of the examination light incident on the detection surface is not parallel to rays of the total reflection light reflected by the detection surface, and the angle between the two light rays is $2\theta_1$ ($\theta_1$ represents the angle of incidence of the examination light). Therefore, the mounting angle between the light source and the photosensor is also $2\theta_1$, and therefore they can not be mounted on a common board in parallel relation to each other (perpendicularly to the board).

However, by changing the direction of the optical path of the examination light (the total reflection light) using the mirrors or the like as described above, the examination light emitted from the light source can be parallel to the total reflection light incident on the photosensor. As a result, the light source and the photosensor can be mounted on the common board in parallel relation to each other.

Here, the above term "mirrors or the like" should be construed as including the detection surface itself in addition to a plane mirror and other mirrors, because the detection surface achieves the same reflection effect as a plane mirror does.

A main portion of the optical path can be constituted by a prism, and the mirrors or the like for changing the direction of the examination light can be formed on outer surfaces of this prism.

Namely, the prism has a plurality of outer surfaces intersecting one another, and these outer surfaces are suitably positioned at suitable angles, respectively, and mirrors or the like for reflecting the examination light are formed on the outer surfaces, respectively, so that the desired optical path can be formed.

Preferably, apertures for allowing only those light rays, incident at a predetermined angle, to pass therethrough are provided in the optical path leading from the light source to the photosensor.

Thanks to the provision of the apertures, disturbance light and noise light (in the examination light) entering at an angle difference from that of the desired examination light, and scattered light in the total reflection light can be removed. As a result, the S/N ratio of the particle concentration detection apparatus is increased, and the detection precision can be enhanced.

For example, apertures are provided respectively in the optical path portion at the light-incident side of the prism and the optical path portion at the light-outgoing side of the prism.

By providing the aperture at the light-incident side, the examination light can be incident on the detection surface at a predetermined angle, while shutting out the noise light.

By providing the aperture at the light-outgoing side, only the regular total reflection light can be caused to be incident on the photosensor, while shutting out the disturbance light and the noise light.

Preferably, in the particle concentration detection apparatus, there is provided a projected portion inserted in a vessel (container) or a conduit or the like for containing the examination-undergoing liquid, and there is provided a fixing member for inserting and fixing the projected portion relative to the vessel or the conduit, and the detection surface is formed on the projected portion.

With this construction, the need for the receiving portion for receiving the examination-undergoing liquid, as well as a Conduit for introducing the examination-undergoing liquid into the receiving portion, is obviated, and the number of the component parts is reduced. Since the vessel or the conduit or the like for containing the examination-undergoing liquid can be attached directly to the associated equipment, the particle concentration detection apparatus can be installed in a space-saving manner.

Preferably, there is provided a confining portion for the cleaning members which portion allows the examination-undergoing liquid to freely flow therethrough.

As described above, the cleaning members are caused to be floated by movement of the examination-undergoing liquid, and can prevent the detection surface from being soiled.

As shown in a formula (1) (representing the index of the depth of entering of an evanescent wave) later described, in case that the wavelength $\lambda$ of the examination light is made large, the angle $\theta_1$ ($\theta_1 > \theta_c$) of incidence of the examination light is made small, and the refractive index of the prism is made low, the rate of change of the total reflection light with respect to the particle concentration, that is, the detection sensitivity, can be enhanced.

For example, where the examination-undergoing liquid is lubricating oil in a diesel engine, the optical system may be constructed in such a manner that an LED or a semiconductor laser for emitting light of red or infrared wavelength (not less than 600 nm) is used as the light source, that the light-emitting portion forming the detection surface is made of glass or a resin capable of allowing light to transmit therethrough, and that the incidence angle $\theta_1$ is set to a value close to the total reflection critical angle $\theta_c$.

BRIEF DESCRIPTION OF THE DRAWINGS

FIG. 5 is a graph showing the relation between the particle concentration and the reflectance in an apparatus for detecting the concentration of particles in a liquid according to the present invention;

DESCRIPTION OF THE PREFERRED EMBODIMENTS

FIRST EMBODIMENT

An apparatus for detecting the concentration of particles in a liquid according to an embodiment of the present invention will now be described with reference to FIGS. 1 to 4E. In this embodiment, the concentration of carbon particles in lubricating oil in a diesel engine is detected so as to judge deterioration of the lubricating oil.

Figure 1:
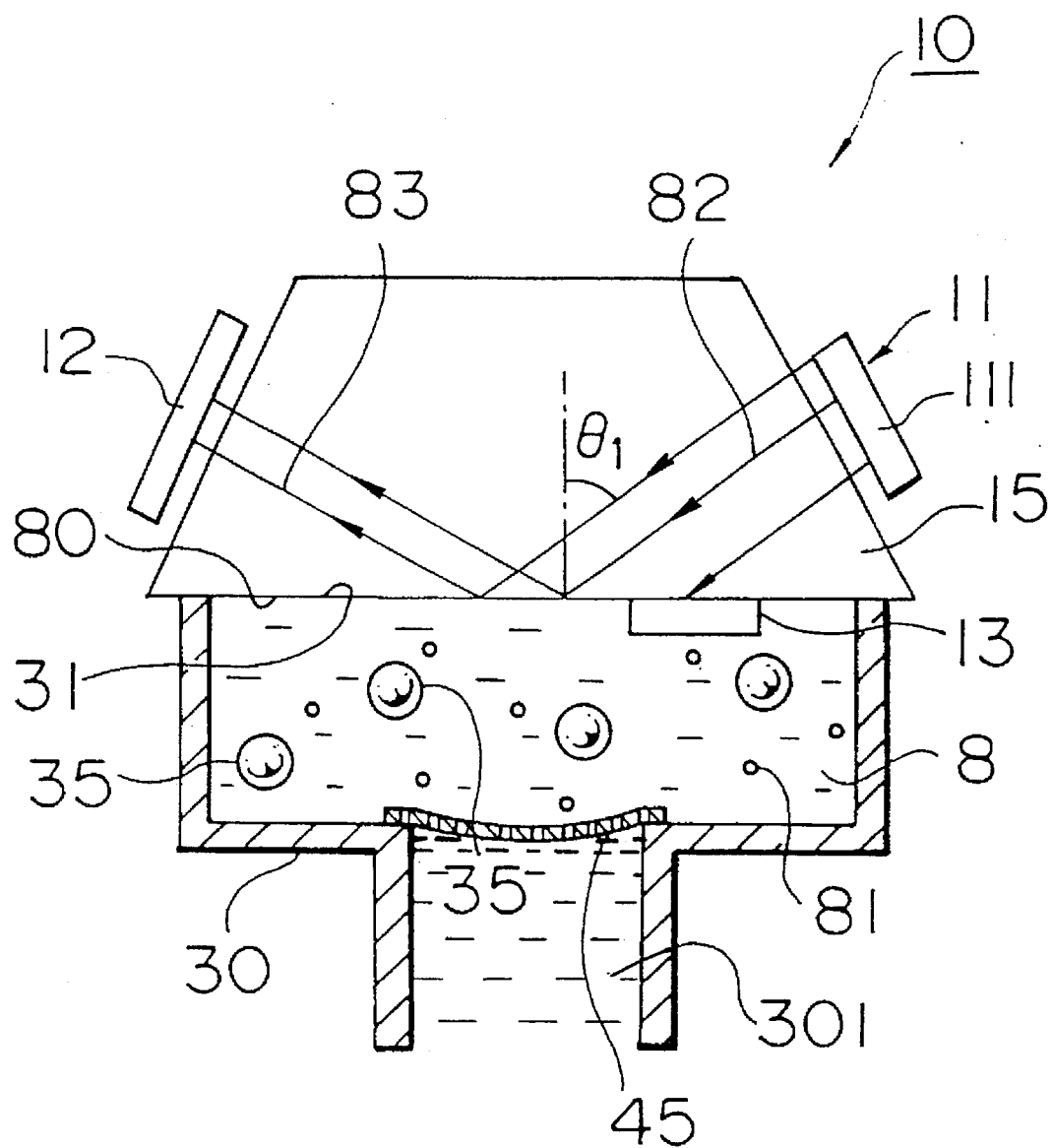
FIG. 1 a view explanatory of an optical system of an oil deterioration detection apparatus of a first embodiment.
Figure 2:
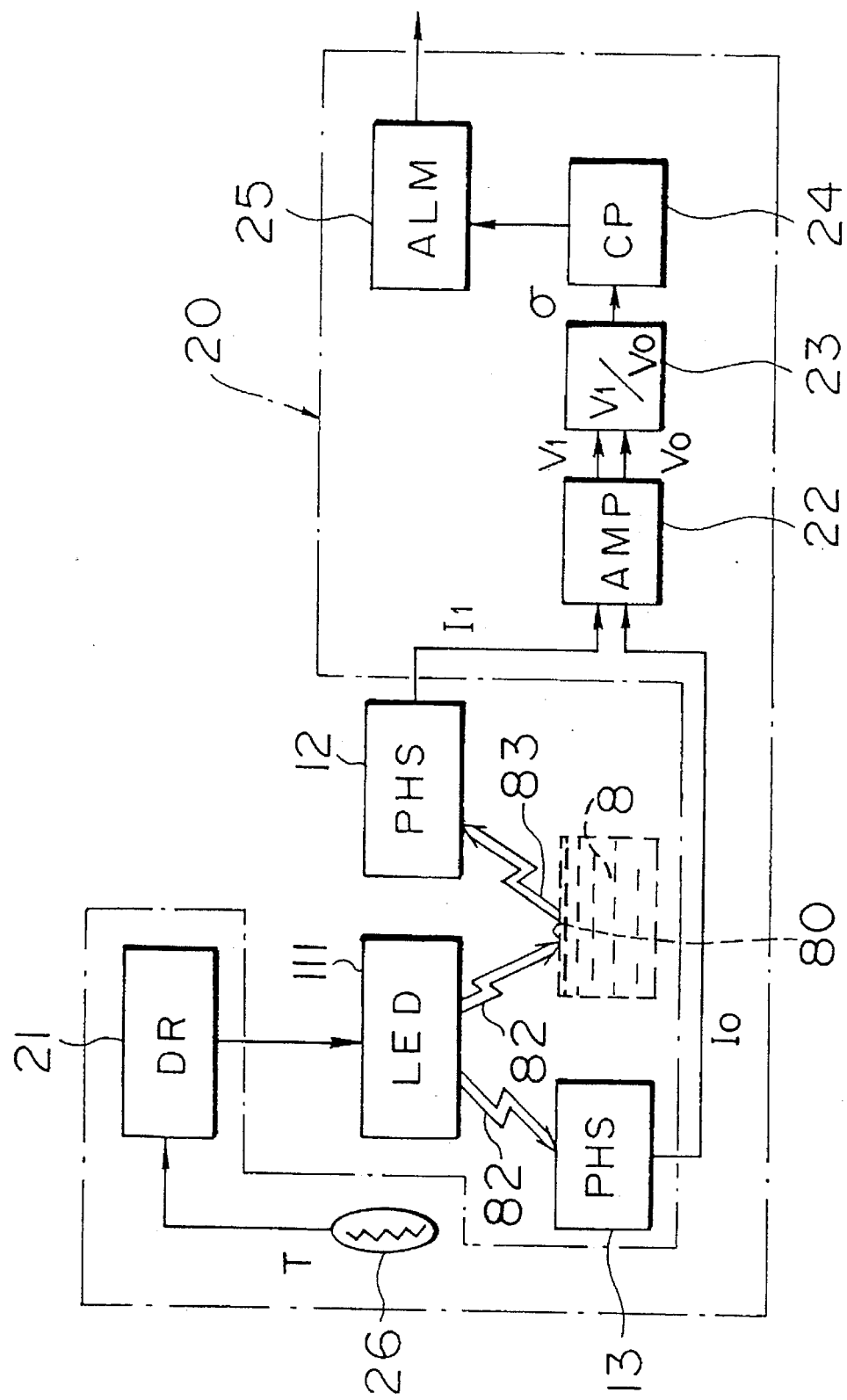
FIG. 2 is an illustration explanatory of the processing of signals in the oil deterioration detection apparatus of the first embodiment.

As shown in FIGS. 1 and 2, an optical system of the carbon particle concentration detection apparatus 10 of this embodiment comprises a light emitting portion 11 for emitting examination light 82 to be totally reflected by a boundary surface 80 contiguous to a liquid 8 to be examined, a photosensor 12 for receiving reflection light 83 from the examination-undergoing liquid 8, a reference photosensor 13 for directly receiving the examination light 82, and a judgment portion 20 for determining reflectance $\sigma$ from output signals of the two photosensors 12 and 13 and for calculating the particle concentration $\alpha$ in the examination-undergoing liquid 8 from this reflectance.

The examination-undergoing liquid 8 in this embodiment is lubricating oil in a diesel engine, and the judgment portion 20 further judges the deterioration of the lubricating oil from the particle concentration $\sigma$.

Cleaning members 35, caused to be floated by the movement of the examination-undergoing liquid 8, are received in a receiving portion 30, which has a detection surface 31 disposed in contact with the examination-undergoing liquid 8, for cleaning the detection surface 31, the examination light 82 being incident on this detection surface 31.

This embodiment will be described in further detail.

The examination light 82, emitted from a light source 111 of the light-emitting portion 11, advances in a prism 15, and is totally reflected on the boundary surface 80 contiguous to the examination-undergoing liquid 8, and the reflection light 83 is incident on the photosensor 12.

More specifically, the relation, $\theta_1 > \sin^{-1}(n_2/n_1)$, is established where $n_1$ represents the refractive index of the prism 15, $n_2$ represents the refractive index of the examination-undergoing liquid 8, and $\theta_1$ represents the angle of incidence of the examination light 82.

The reference photosensor 13 is mounted on one side portion of the detection surface 31 of the receiving portion 30, and is in contact with the prism 15. The reference photosensor 13 is a photosensor for detecting the intensity of the examination light 82. According to this arrangement, a change of intensity of emission of the light-emission source due to change of temperature, and a change of light-emission source with the passage of time can be cancelled, thereby improving an accuracy of measurement.

The receiving portion 30 for holding the examination-undergoing liquid 8 therein has a flow inlet portion 301 for the liquid 8, a flow outlet portion (not shown) for the liquid 8, and the detection surface 31 for the examination light 82, as shown in FIG. 1.

A flow-out prevention member 45 in the form of a metal net for preventing the cleaning members 35 from flowing out of the receiving portion 30 is provided in each of the flow inlet portion 301 and the flow outlet portion. The mesh of the flow-out prevention member 45 is smaller than the size of the cleaning members 35.

Figure 4A:
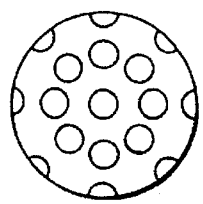
FIGS. 4A to 4E are views explanatory of various configurations of a cleaning member in the oil deterioration detection apparatus of the first embodiment.
Figure 4B:
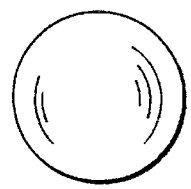
Figure 4C:
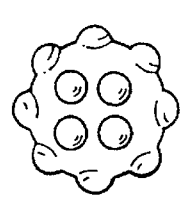
Figure 4D:
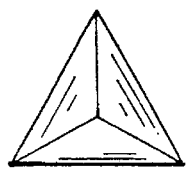
Figure 4E:
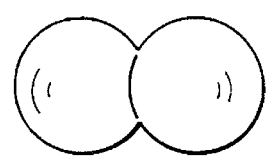

The cleaning members 35, together with the examination-undergoing liquid 8, in the receiving portion 30 are made of fluoroplastics or the like so that they do not damage the prism 15, and are durable in the examination-undergoing liquid 8. They may be, for example, in the form of a spherical body having semispherical small recesses (FIG. 4A), a spherical body (FIG. 4B), a spherical body having small spherical projections (FIG. 4C), a regular tetrahedral body (FIG. 4D), or a body formed generally by combining two spherical bodies together (FIG. 4E).

Any of these cleaning members 35 has such configuration and specific gravity that it can easily move in response to the movement of the examination-undergoing liquid 8.

As the material for the cleaning member 35, other material than fluoroplastics, such as fluoro-rubber, glass, ceramics and metal, can be used. Also, the cleaning member 35 may be of a hollow so as to obtain the required specific gravity.

It is also preferred that the surface of the cleaning member 35 should have a low light reflectance. To meet these requirements, the surface portion of the cleaning member may be formed of a material different from that of a core portion thereof. For example, a polytetrafluoroethylene ball having an iron core portion coated with polytetrafluoroethylene, or a fluororubber ball having an iron core portion coated with fluoro-rubber can be used.

Figure 3:
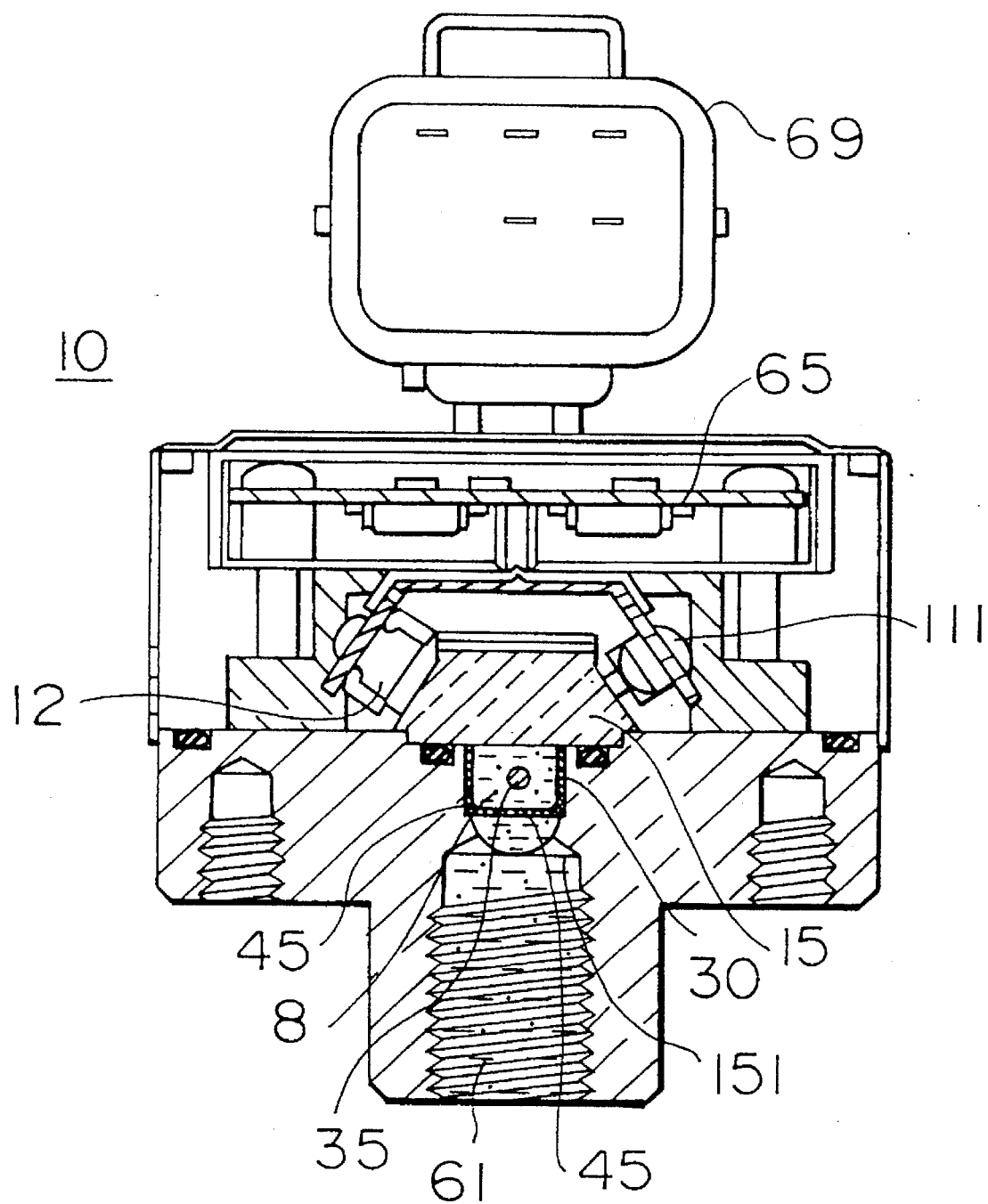
FIG. 3 is a front-elevational, cross-sectional view of the oil deterioration detection apparatus of the first embodiment.

The whole of the particle concentration detection apparatus 10 has a cross-sectional shape shown in FIG. 3. The optical members including the prism 15 are provided at a central portion of the apparatus, and a feed conduit 61 for the examination-undergoing liquid 8 is provided at below of the prism 15, and the receiving portion 30 communicated with a discharge conduit (not shown) disposed perpendicular to the feed conduit 61.

A printed circuit board 65, having the judgment portion 20 mounted thereon, is provided at an upper portion of the apparatus. In FIG. 3, a reference numeral 69 denotes an input/output connector for signals and power.

The examination-undergoing liquid 8 flows through the receiving chamber 30 from the feed conduit 61, and flows out from the discharge conduit (not shown).

The examination-undergoing liquid 8 in the receiving portion 30 is in contact with the prism 15.

The photosensor 12 and the light source 111 are mounted respectively on side surfaces of the prism 16, and the reference photosensor 13 (not shown in FIG. 3) is mounted on a bottom surface of the prism 15.

As shown in FIG. 2, the judgment portion 20 comprises a driver circuit 21 for driving an LED (light source 111), a signal amplifier 22 for amplifying an output signal $I_1$ of the photosensor 12 and an output signal $I_0$ of the reference photosensor 13, a divider circuit 23 for dividing an amplified output $V_1$ of the photosensor 12 by an amplified output $V_0$ of the reference photosensor 13 to obtain the reflectance $\sigma$, a judgment circuit 24 for comparing the reflectance $\sigma$ ($=I_1/I_0$) with a reference reflectance $\sigma_s$ to judge the deterioration of the lubricating oil, and a driver circuit 25 for driving an alarm display device (not shown). The judgment circuit 24 may convert the reflectance $\sigma$ into the particle concentration $\alpha$ in accordance with a characteristic diagram of FIG. 5, thus outputting it.

A thermistor temperature gauge 26 is provided in the vicinity of the boundary surface 80 of the prism 15, and output signal T of the temperature gauge is inputted to the above driver circuit 21.

The driver circuit 21 operates the light source 111 only when the temperature output signal T is within a predetermined range between $T_1$ and $T_2$.

Therefore, the particle concentration is measured only when the temperature of the lubricating oil is within the predetermined range, and then an error due to a temperature change of the lubricating oil hardly occurs.

The output signal $I_1$ of the photosensor 12 receiving the reflection light 83 is amplified, and then is divided by the output signal $I_0$ of the reference photosensor 13 to be converted into the reflectance $\sigma$. Therefore, even if the intensity of the light from the light source 111 is varied, a detection error will not occur.

Next, the operation of the cleaning members 35 will now be described.

The examination-undergoing liquid 8 flows in a predetermined direction, and convection is also produced within the receiving portion 30. On the other hand, the cleaning members 35 are confined within the receiving portion 30 by the flow-out prevention member 45. Therefore, the cleaning members 35 are caused to move in the receiving portion 30 by the force of the examination-undergoing liquid 8. Therefore, the cleaning members 35 collide on the detection surface 31 (which defines the boundary surface between the prism 15 and the examination-undergoing liquid 8) to destroy and separate soils from the detection surface 31.

The cleaning members 35 also serve to prevent soils from growing on the detection surfaces.

In this embodiment, without providing any special soil-removing mechanism, such as a wiper, on the detection surface 31, soils on the detection surface 31 can be removed with the relatively simple construction in which the cleaning members 35 are received in the receiving portion 30.

As described above, in this embodiment, there is provided the particle concentration detection apparatus 10 in which the boundary portion (detection surface 31) between the prism 15 and the examination-undergoing liquid 8 can be prevented from being soiled, and also soils on this boundary portion can be removed.

If the movement of the liquid in the flow path is promoted, for example, by a means for intermittently applying an impulse stream to the examination-undergoing liquid 8, this is more effective.

The particle concentration detection apparatus 10 of this embodiment measures the totally-reflected light 83, and detects the particle concentration, and therefore can achieve the purpose regardless of whether the light transmittance of the examination-undergoing liquid 8 is high or low.

Therefore, even for the examination-undergoing liquid 8 of a low light transmittance, the particle concentration can be measured precisely.

Besides, even if non-particle foreign matters such as bubbles exit in the examination-undergoing liquid 8, this hardly affects the measurement, as described above.

Furthermore, since the soil of the detection surface 31 can be suppressed by the cleaning members 35, an error due to the soil of the detection surface 31 hardly occurs.

As described above, in this embodiment, there is provided the particle concentration detection apparatus 10 which is not lowered in sensitivity even for the liquid of a low light transmittance, and is hardly affected by non-particle foreign matters such as bubbles, and can suppress an error due to the soil of the detection surface 31.

In this embodiment, although the thermistor temperature gauge 26 is provided in the vicinity of the examination-undergoing liquid 8 so as to measure the particle concentration of the examination-undergoing liquid in the predetermined temperature range, the thermistor temperature gauge 26 may be provided near to the light source 111 so as to suppress the operating ambient temperature of the LED (light source 111) to below a predetermined temperature (for example, 100° C.), thereby prolonging the lifetime of the LED.

A measurement principle will be described hereinafter.

Figure 6:
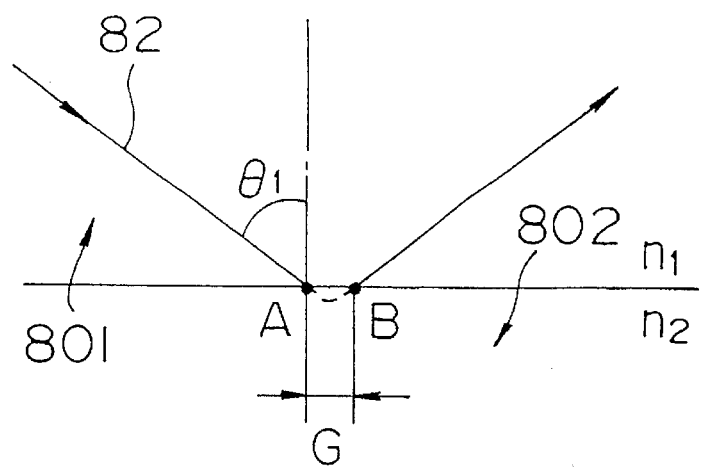
FIG. 6 is an illustration explanatory of an evanescent wave.

As shown in FIG. 6, when the light advances from a first medium 801 with a refractive index $n_1$ to a second medium 802 with a refractive index $n_2$ at an angle $\theta_1$ larger than a total reflection critical angle $\theta_c$, the light will not enter the second medium 802 with the refractive index $n_2$, but will be totally reflected. However, upon observing this phenomenon in detail, the reflection light goes out from a point B apart from a point A of incidence by a distance G.

Namely, the light once enters the second medium 802, and goes out from the point B as shown in a broken line in FIG. 6. This entering light is called "evanescent wave", and the gap G is called "Goos-Hänchen shift".

Figure 7:
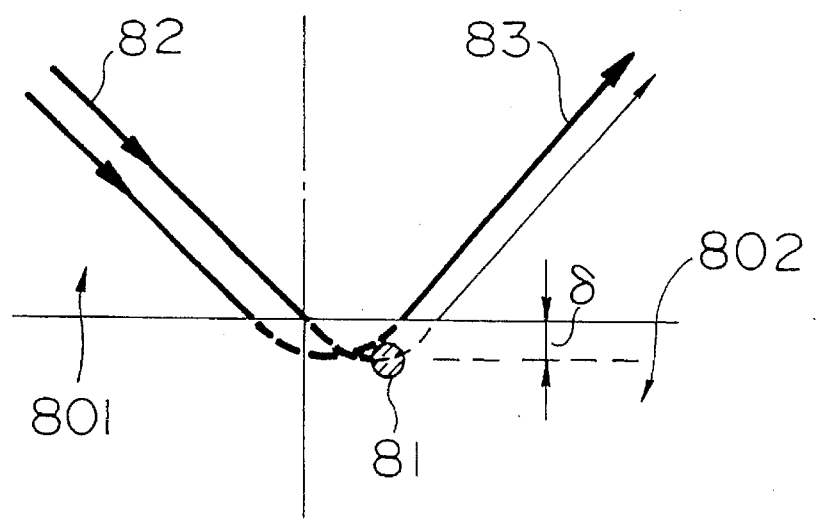
FIG. 7 is an illustration explanatory of the principle of the optical system of the particle concentration detection apparatus of the present invention.

If a solid foreign matter 81 such as carbon exists in the second medium 802, the evanescent wave is subjected to absorption and scattering, so that the intensity of the totally reflected light decreases, as shown in FIG. 7.

Incidentally, the depth of entering of the light into the second medium 802 varies depending on a wavelength $\lambda$ of the light, the refractive indexes $n_1$ and $n_2$ of the mediums 801 and 801, the angle $\theta_1$ of incidence and etc. Namely, the entering depth D at which the intensity of the electric field of the evanescent wave is attenuated to 1/e is expressed by the following formula:

$$D = \lambda \times \{2\pi(n_1^2 \sin^2\theta_1 - n_2^2)^{1/2}\} \quad (1)$$

The greater the depth D of entering of the evanescent wave is, the larger the absorption and scattering (caused by the presence of the solid foreign matter 81) are, and therefore the degree of change (decrease) (i.e., rate of change) of the totally reflected light increases.

In the present invention, the concentration of the particles in the examination-undergoing liquid is detected utilizing the above phenomenon.

Namely, the reflection light 83, totally reflected by the boundary surface contiguous to the examination-undergoing liquid, is attenuated in proportion to the particle concentration of the liquid, as shown in FIG. 5, and therefore the particle concentration of the examination-undergoing liquid can be detected by the degree of decrease of the intensity of the reflection light, that is, the change of the reflectance.

In this case, in order that the number of particles in the liquid up to the depth $\delta$ ($=\lambda/2$) of entering of the evanescent wave will not be varied, a suitable area S of the detection surface as well as a suitable sampling time period T (time period of measuring of the amount of the received light) at the judgment portion, is selected in accordance with the particle concentration. Namely, the number of particles in a volume $S \times \delta$ at the detection surface of the examination-undergoing liquid is controlled so as not to be varied during the sampling time period T, and by doing so, variations in measuring precision are eliminated.

In the present invention, the reflection light from the examination-undergoing liquid is detected so as to detect the particle concentration, and therefore this detection is not influenced by whether the light transmittance of the examination-undergoing liquid is high or low. Therefore, the sensitivity is not lowered at all even for the examination-undergoing liquid of a low transmittance.

Besides, even if bubbles or the like are present in the examination-undergoing liquid, the evanescent wave is hardly affected. Namely, the depth $\delta$ of entering of the evanescent wave is extremely shallow, and therefore the probability that the evanescent wave impinges on a bubble is extremely low, and even if the evanescent wave impinges on a non-particle foreign matter such as a bubble, this wave will hardly be scattered by a bubble.

Figure 13:
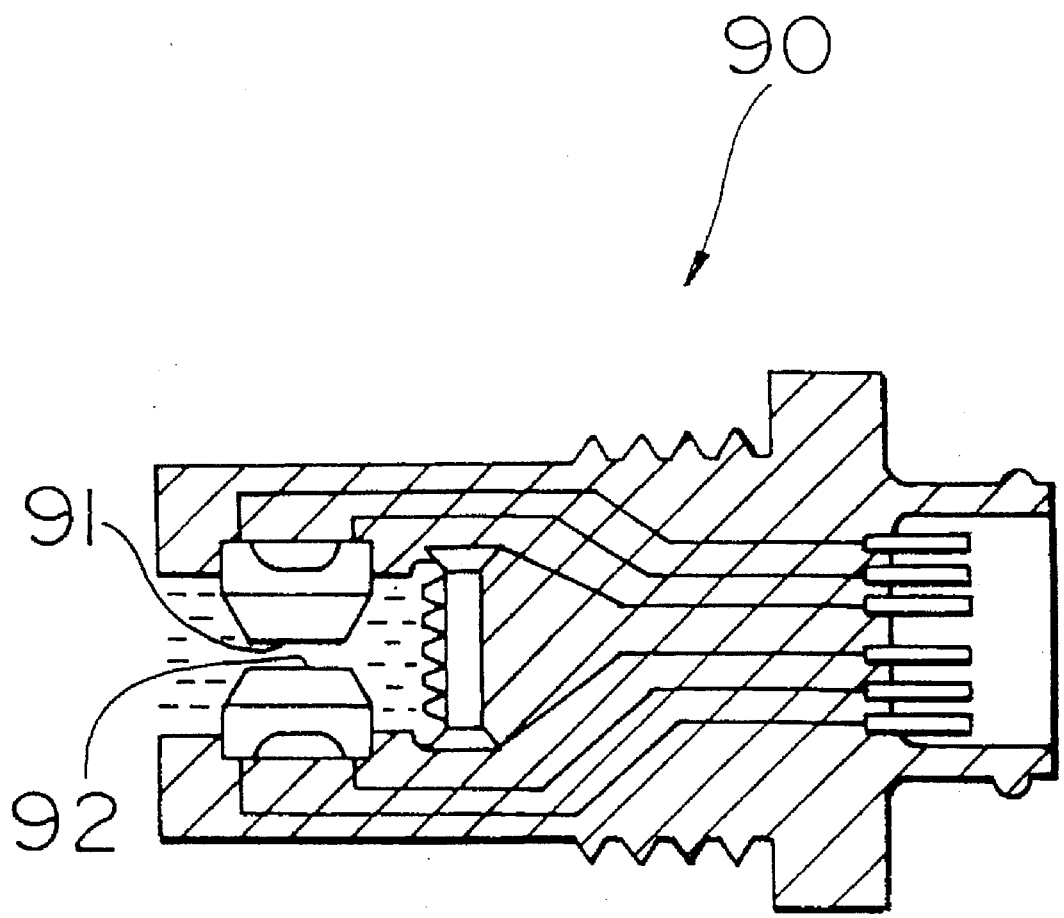
FIG. 13 is a view explanatory of a conventional oil deterioration detection apparatus.

In a conventional particle concentration detection apparatus 90 of the transmittance type (FIG. 13), particles deposit on two surfaces, that is, a light-emitting surface 91 and a light-receiving surface 92, thus decreasing the amount of light received by a photosensor. In the present invention, however, there is provided only one detection surface, and therefore such adverse effect can be reduced to a half level.

Since the apparatus of the present invention is of the reflection type, the depth of the receiving portion for receiving the examination-undergoing liquid can be increased. In the transmittance type, the amount of transmission of light is decreased as the depth of the examination-undergoing liquid is enlarged. With this construction of the present invention, the cleaning members can be received in the receiving portion, so that the soil of the detection surface can be suppressed.

Furthermore, since the apparatus of the present invention is of the reflection light-measuring type, the presence of the cleaning members, as well as the presence of bubbles, will hardly affect the detection precision. Even if the presence of the cleaning members slightly affects the amount of the received light, the influence of the cleaning members can be made uniform by increasing the sampling time period T at the judgment portion, and therefore the measuring precision will not be affected.

As described above, in the present invention, there is provided the particle concentration detection apparatus which is not lowered in sensitivity even for the liquid of a low light transmittance, and is hardly affected by non-particle foreign matters such as bubbles.

Second Embodiment

Figure 8:
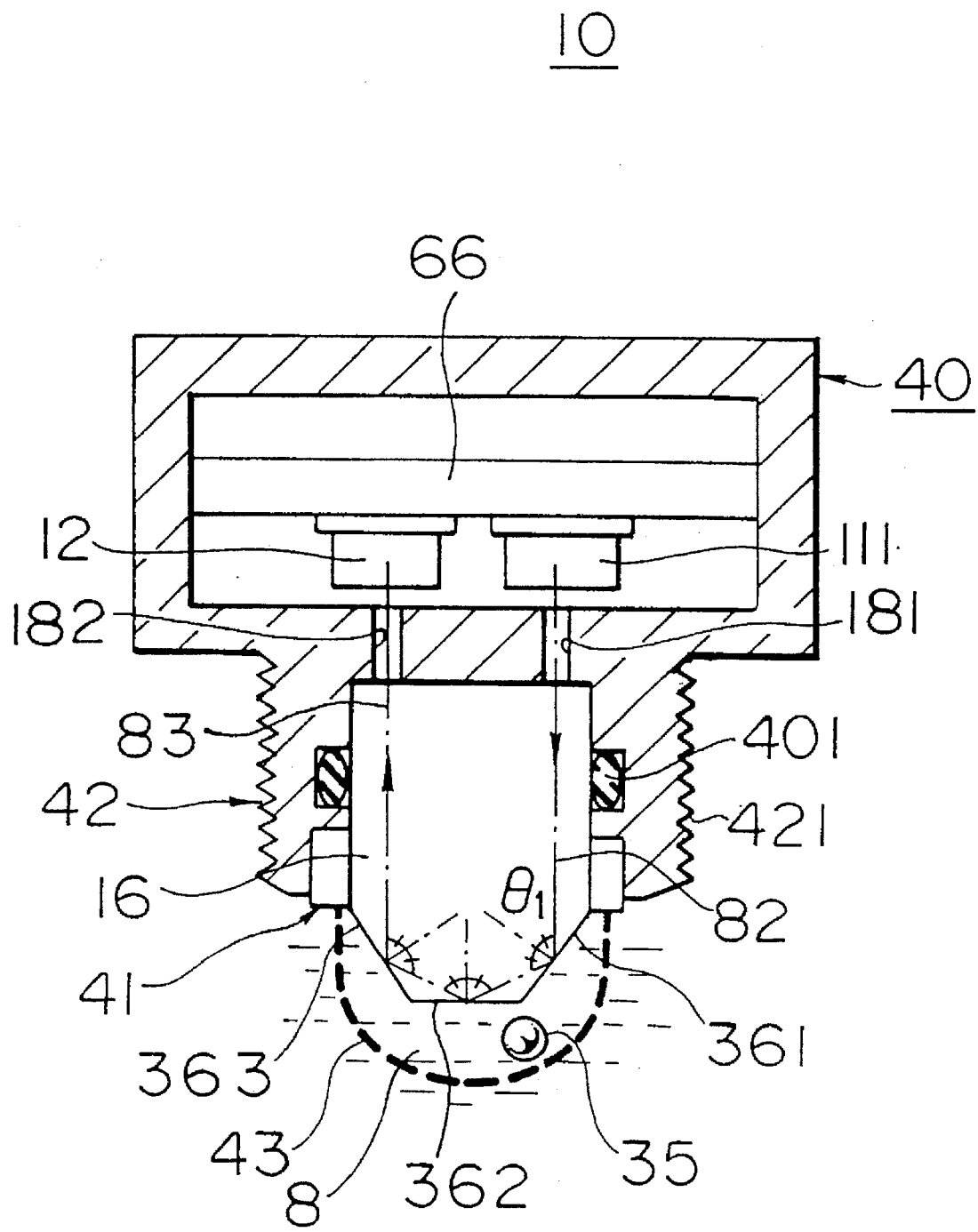
FIG. 8 is a cross-sectional view of an oil deterioration detection apparatus of a second embodiment.

As shown in FIG. 8, this embodiment differs from the first embodiment mainly in that there are provided three detection surfaces 361 to 363 disposed in contact with an examination-undergoing liquid 8 for totally reflecting examination light 82 at boundary surfaces thereof, and that the detection surfaces 361 to 363 are inserted in and fixed to a vessel or a conduit or the like holding the examination-undergoing liquid 8.

The direction of the optical path of the examination light 82 from a light source 111 is changed by the detection surfaces 361 to 363, and is incident on the photosensor 12 mounted on a board 66 having the light source 111 mounted thereon.

The detection surfaces 361 to 363 are formed respectively on outer surfaces of a prism 16 housed in a projected portion 41.

An aperture 181 through which the only examination light 82 advancing at a predetermined angle passes is provided in the optical path at the light-incident side of the prism 16, and an aperture 182 through which the only reflection light 83 at a predetermined angle passes is provided in the optical path at the light-outgoing side of the prism 16.

As shown in FIG. 8, the particle concentration detection apparatus 10 includes the projected portion 41 for being inserted in a vessel or a conduit or the like for holding the examination-undergoing liquid 8, and a fixing member 42 for inserting and threadedly fixing the projected portion 41 relative to the vessel or the conduit. A confining portion 43 for confining cleaning members 35 is provided on the projected portion 41, which covers the detection surfaces 361 to 363 and allows the examination-undergoing liquid 8 to freely pass therethrough. The cleaning members 35, caused to float by the movement of the examination-undergoing liquid 8, are received within the confining portion 43.

In this embodiment, the wavelength λ of the examination light 82 is 940 nm, and the examination-undergoing liquid 8 is engine oil in a diesel engine, and its refractive index $n_2$ is 1.48 (at λ=940 nm).

The prism 16 may be made of a material whose refractive index $n_1$ is 1.73 or more (at λ=940 nm) and whose chemical resistance is excellent. Such material includes FDS30, FD110, FF9, FD60 and NbFD15 which are productions of HOYA CORPORATION. A total reflection critical angle $θ_{cl}$ is 56° if the refractive index of the engine oil is 1.46, and is 58.5° if the refractive index of the engine oil is 1.50.

The three detection surfaces 361 to 363 are formed on the outer surfaces of the prism 16 in such a manner that the angle between any two adjacent ones of these detection surfaces is 120°.

The examination light 82 emitted from the light source 111 passes through the first aperture 181, and enters the prism 16, and is incident on the first detection surface 361 at an incidence angle $θ_1$ of 60°.

The examination light is totally reflected by the first detection surface, and is incident on the second detection surface 362 at an incidence angle of 60° to be again totally reflected by it, and then is incident on the third detection surface 363 at an incidence angle of 60°. The examination light 82 is again totally reflected by this third detection surface, and is incident on the photosensor 12 through the second aperture 182. Thus, the optical path is formed in this manner.

As will be appreciated from FIG. 8, the direction of the reflection light 83 incident on the photosensor 12 is opposite (that is, 180° different from) and parallel to the direction of the examination light 82 emitted from the light source 111, and the light source 111 and the photosensor 12 are juxtaposed on the board 66 in parallel relation to each other, and are disposed perpendicular to the board 66.

Circuits components of a reference sensor and a judgment portion (not shown) are also mounted on the board 66.

The confining portion 43 for the cleaning members 35 is provided on the projected portion 41 in covering relation to the detection surfaces 361 to 363. The confining portion 43 is made of a metal net, and is of such a configuration that the cleaning members 35 can be moved effectively.

An externally-threaded portion 421 is formed on the surface of the fixing member 42, and is threadedly engaged in a threaded hole formed in the vessel or the conduit (not shown) holding the examination-undergoing liquid 8, thereby attaching the particle concentration detection apparatus 10 to the associated equipment.

The vessel or the conduit or the like is, for example, an engine oil passageway portion (such as a bracket of an oil filter) or an oil pan.

In FIG. 8, reference numeral 40 denotes a housing of the particle concentration detection apparatus 10, and reference numeral 41 denotes an O-ring for liquid sealing.

Advantages of this embodiment will now be described.

In the particle concentration detection apparatus of this embodiment, there are provided the three detection surfaces 361 to 363, and the totally reflected light at each of the three detection surfaces 361 to 363 is changed (decreased) in accordance with the particle concentration of the liquid. Therefore, the rate of change of the amount of received light corresponding to the particle concentration detected by the photosensor 12 is increased generally algebraically, as compared with the case where only one detection surface is provided.

As a result, the sensitivity of detection of the particle concentration is greatly enhanced.

The examination light 82 is incident at an angle of 60° on each of the three detection surfaces 361 to 363 different from one another by 120°, thereby changing the direction of the optical path. As a result, the direction of the total reflection light 83 reaching the photosensor 12 is 180° opposite to the direction of the examination light 82 emitted from the light source 111.

Therefore, the light source 111 and the photosensor 12 can be juxtaposed or arranged totally parallel to each other, and can be mounted on the common board 66. In the first embodiment, the mounting angle of the light source 111 is different from that of the photosensor 12, and therefore they can not be mounted on the common board as shown in FIGS. 1 and 3. Therefore, in this embodiment, the two members 111 and 12, as well as the circuit components of the judgment portion, can be mounted on the single board 66, and time and labor required for mounting the parts can be greatly reduced.

The particle concentration detection apparatus of this embodiment can be directly installed to the vessel or the conduit holding the examination-undergoing liquid 8, through the fixing member 42, and therefore this apparatus does not need to be provided with a receiving portion (as at 30 in FIG. 1) or a conduit portion for receiving the examination-undergoing liquid 8, so that the number of the component parts is reduced. Besides, since this apparatus is attached to the vessel or the conduit or the like, the installation space is reduced.

Since the apertures 181 and 182 are provided respectively on the light-incident side and light-outgoing side of the prism, the intrusion of noise light and scattered light can be avoided, and therefore the S/N ratio is improved, thus enhancing the precision.

Third Embodiment

Figure 9:
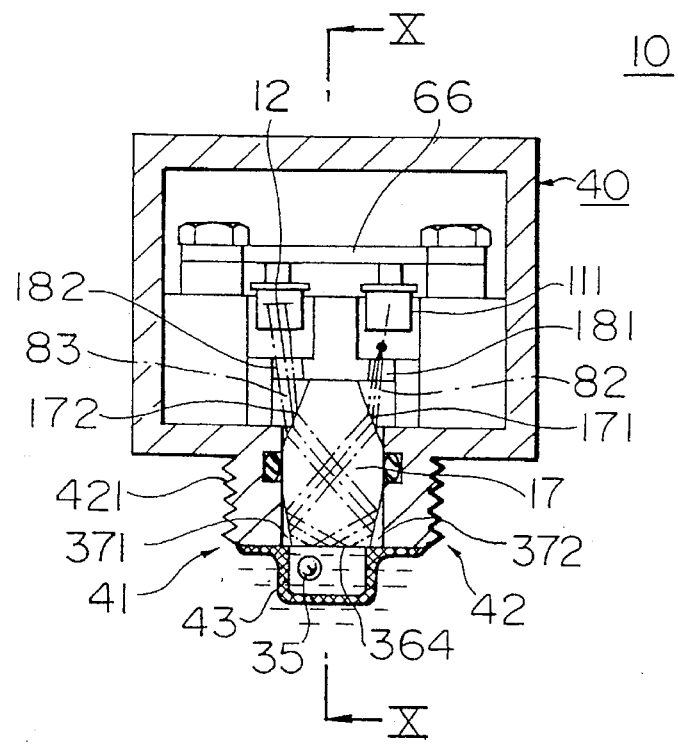
FIG. 9 is a cross-sectional view of an oil deterioration detection apparatus of a third embodiment.

In this embodiment, as shown in FIG. 9, one detection surface 364 and two mirrors 371 and 372 are formed respectively on outer surfaces of a prism 17.

More specifically, examination light 82 emitted from a light source 111 is incident on an incident surface 171 of the prism 17, and then is reflected by the first mirror (plane mirror) 371, and is incident on the detection surface 364.

The light is totally reflected by the detection surface 364, and is again reflected by the second mirror (plane mirror) 372, and then goes out from an outgoing surface 172, and is incident on a photosensor 12.

The prism 17 may be made of a material whose refractive index $n_1$ is 1.51 or more (at $\lambda=940$ nm) and whose chemical resistance is excellent. Such material includes FF5 which is a production of HOYA CORPORATION. A total reflection critical angle $\theta_c$ is 67.8° if the refractive index of the engine oil is 1.46, and is 72° if the refractive index of the engine oil is 1.50.

The incidence angle with respect to the detection surface 364 is more than a total reflection critical angle $\theta_{c2}$, and is 67.8° or 72° close to it.

The examination light 82 emitted from the light source 111 is generally parallel to the reflection light 83 incident on the photosensor 12, and the light source 111 and the photosensor 12 are mounted on a common board 66.

Figure 10:
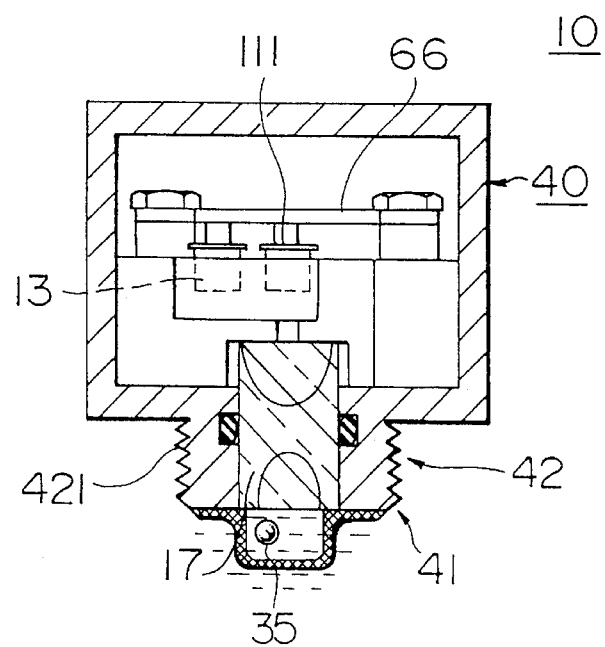
FIG. 10 is a cross-sectional view taken along the line X—X of FIG. 9, with a confining portion omitted.

A reference photosensor 13 is mounted on the board 66 as shown in FIG. 10. The reference photosensor 13 is a photosensor for detecting the intensity of the examination light 82. According this, a change of intensity of emission of the light-emission source due to change of temperature, and a change of light-emission source with the passage of time can be cancelled, thereby improving an accuracy of measurement. Circuit components of a judgment portion (not shown) are also mounted on the board 66.

Fourth Embodiment

Figure 11:
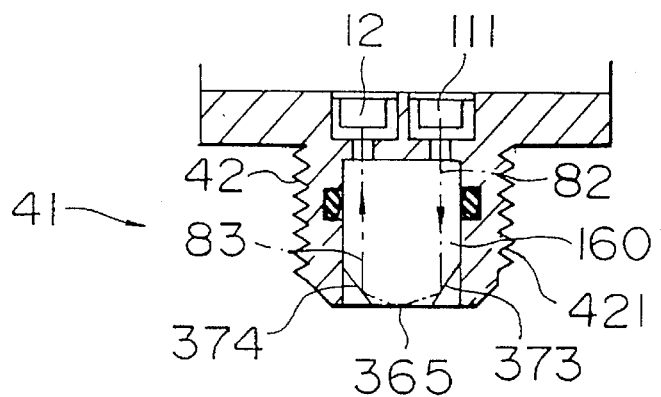
FIG. 11 is a cross-sectional view of an important portion of an optical system of an oil deterioration detection apparatus of a fourth embodiment.

This embodiment differs from the second embodiment in that the first and third detection surfaces 361 and 363 (FIG. 8) of the prism 16 of the second embodiment are replaced by mirrors 373 and 374, respectively, as shown in FIG. 11.

Namely, although an optical path in the particle concentration detection apparatus of this embodiment is the same as that in the second embodiment, this embodiment is different from the second embodiment in that there is provided only one detection surface 365, and that the mirrors 373 and 374 are respectively plane mirrors not in contact with the examination-undergoing liquid.

Fifth Embodiment

Figure 12:
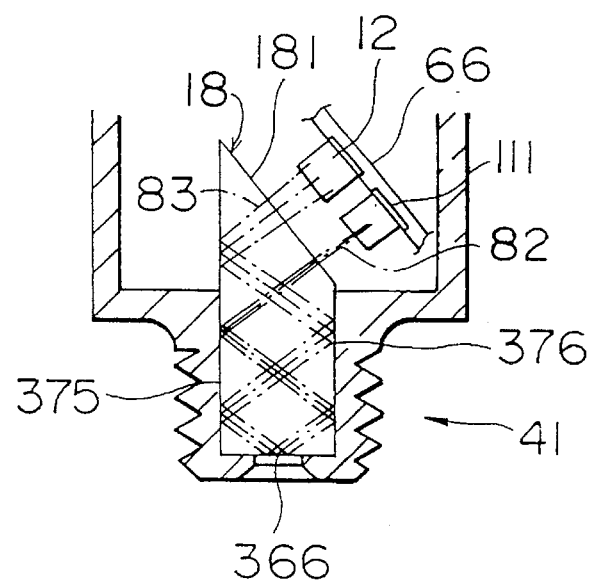
FIG. 12 is a cross-sectional view of an important portion of an optical system of an oil deterioration detection apparatus of a fifth embodiment.

As shown in FIG. 12, this embodiment differs from the third embodiment in that a prism 18 of a different shape is used, and that two mirrors 375 and 376 are mounted respectively on outer surfaces of the prism 18 to form such an optical path that examination light 82 can be reflected a plurality of times by each of these mirrors 375 and 376.

Namely, as shown in FIG. 12, the examination light 82 is reflected by the first and second mirrors 375 and 376, and is incident on a detection surface 366. Reflection light totally reflected by the detection surface 366 is reflected by the first mirror 375 and the second mirrors 376, and then is again reflected by the first mirror 375, and is incident on a photosensor 12.

A light-incident/outgoing surface 181 of the prism 18 is a slanting surface not parallel to the detection surface 366, and a board 66 is disposed parallel to the light-incident/outgoing surface 181.

Sixth Embodiment

This embodiment is directed to an oil deterioration detection apparatus which is installed to a bypass oil passageway connected to an oil circulating line of a gasoline engine.

Figure 14:
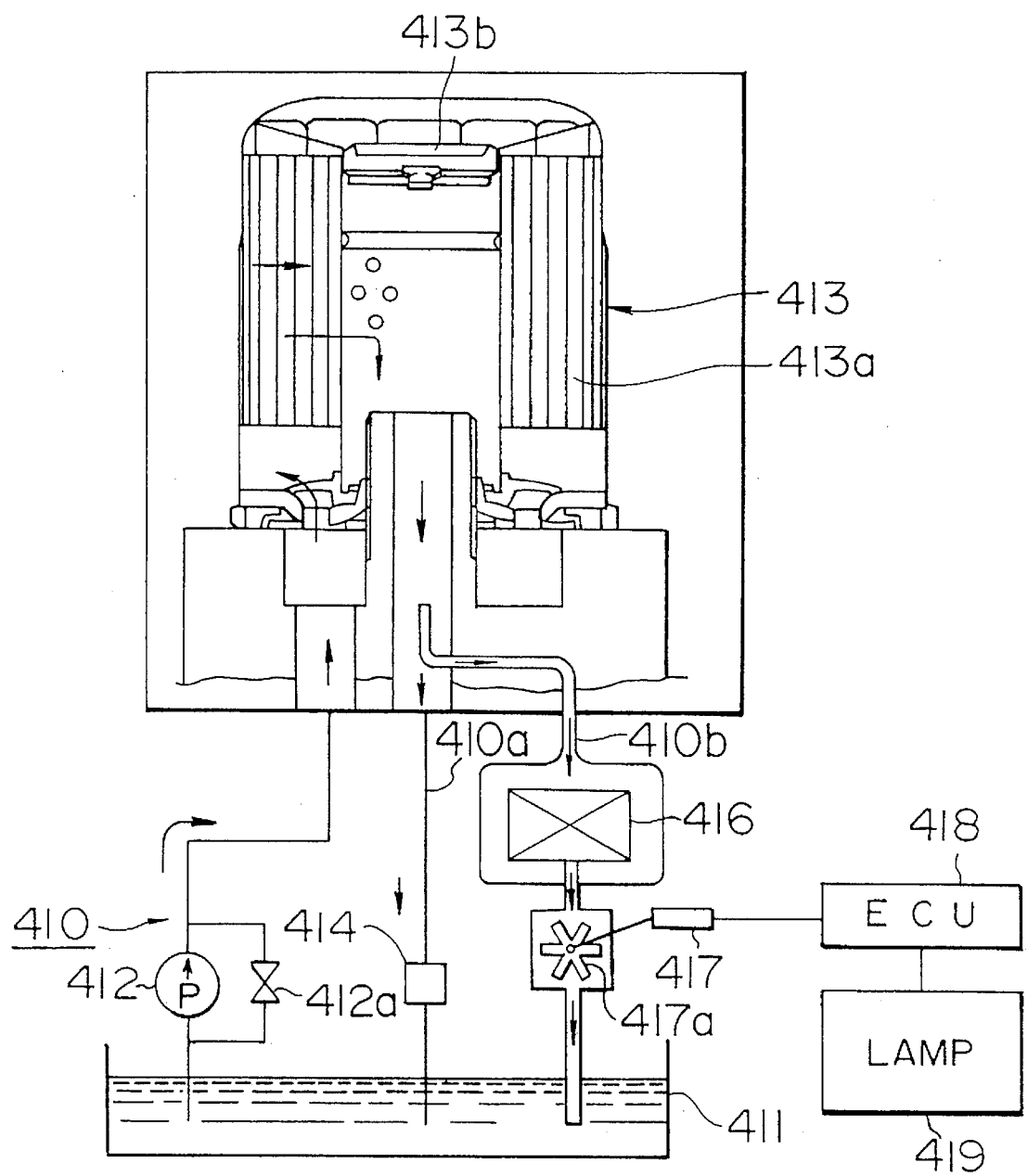
FIG. 14 is a view showing a general construction of a sixth embodiment.

As shown in FIG. 14, the oil circulating line 410 is a line for feeding oil to engine lubricating portions 414. An oil pan 411, an oil pump 412, an oil filter 413 and the engine lubricating portions 414 are provided on this line. Imide succinate serving as a detergent-dispersant is added to the oil.

The oil pump 412 draws the oil stored in the oil pan 411, and feeds it to the oil filter 413. When the pressure at a delivery side of the oil pump 412 exceeds a predetermined level, a control valve 412a, provided parallel to the oil pump 412, is opened to communicate with a suction side of the oil pump 412, thereby adjusting the pressure of the delivery side to the predetermined level.

The oil filter 413 is of the full-flow type, and therefore filters all of the oil discharged from the oil pump 412. A relief valve 413b is provided in the oil filter 413 in view of the filter clogging and a cold start of the engine. A filter element 413a used in the oil filter 413 is formed into a relatively coarse mesh (5 µm–30 µm). The oil passes through the element 413a, and is supplied to the engine lubricating portions 414 through an oil line 410a.

The engine lubricating portions 414 include bearings, sliding portions and the like in the engine which need to be reduced in friction and wear at their friction surfaces.

The oil from the engine lubricating portions 414 passes through the oil filter 413, so that undissolved components of a size larger than a predetermined size, such as wear powder, combustion products and deteriorated components resulting from the oil itself, are removed by the filter 413, thereby purifying the oil. Thereafter, the purified oil is again fed to the engine lubricating portions 414. Here, the term "predetermined size" means a size of the mesh of the filter element 413a.

A bypass oil line 410b branches from the oil circulating line 410 intermediate the delivery side of the oil filter 413 and the engine lubricating portions 414, and is connected to the oil pan 411. The oil deterioration detection apparatus of the present invention is provided on this bypass oil line 410b.

The oil deterioration detection apparatus comprises a fine undissolved component-arresting filter 416, and a flow rate measurement portion 417 serving as an oil deterioration detection means. The oil deterioration detection apparatus cooperates with an engine control unit (ECU) 418 which is provided for the engine and an alarm lamp 419 to form an oil deterioration alarm apparatus.

The fine undissolved component-arresting filter 416 has a mesh which is larger than micelles of the detergent-dispersant added to the oil, and is smaller than the mesh of the filter element 413a. In this embodiment, since imide succinate is used as the detergent-dispersant, the mesh of the arresting filter 416 is more than 1.5 μm (which is the size of the micelles formed by the imide succinate), and is smaller than the mesh (5 μm–30 μm) of the element 413a. In order to arrest the fine undissolved components more effectively, the mesh of the arresting filter 416 is preferably set to a value close to the size of the micelles.

The flow rate measurement portion 417 is provided downstream of the fine undissolved component-arresting filter 416, and counts the pulse produced by a gear 417a rotated by the oil passed through the fine undissolved component-arresting filter 416 and outputs as the flow rate. The flow rate of the oil decreases with the increase of the amount of fine undissolved components arrested by the fine undissolved component-arresting filter 416, and therefore the amount of the fine undissolved components can be determined in view of the detected flow rate of the oil.

The ECU 418 is equipped with an arithmetic and control circuit of a known construction, and inputs the pulses from the flow rate measurement portion 417 and feeds an output to the alarm lamp 419.

The alarm lamp 419 is mounted on a dashboard (not shown) in front of a driver's seat of an automobile, and is lit in response to the output from the ECU 418. Instead of the alarm lamp 419, other alarm device such as an alarm buzzer may be used.

Figure 15:
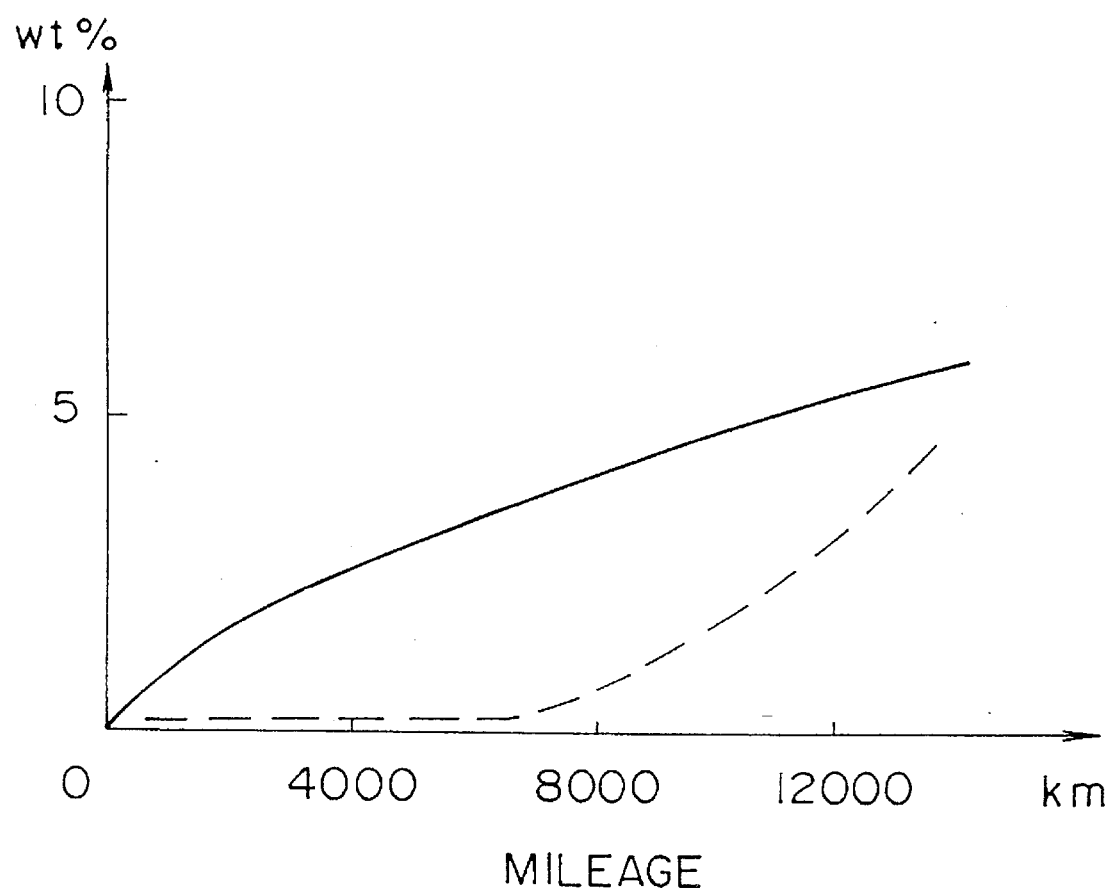
FIG. 15 is a graph showing the relation between the amount of fine undissolved components and a running distance.

In a graph of FIG. 15, a solid line represents the relation between the amount of the fine undissolved components, arrested by the fine undissolved component-arresting filter 416, and a mileage of the automobile. As is clear from this graph, the amount of the fine undissolved components increases generally linearly with the increase of the mileage. The fine undissolved components include those produced by the inclusion of wear powder, sand and fuel into the oil, those produced by the formation of combustion products and the oxidation of the base oil, and those produced by the consumption of additives. Therefore, using the amount of these fine undissolved components as an index, the n-pentane undissolved components, the viscosity and the increase of the total acid value, and the decrease of the total basic value (which are conventional deterioration indexes) can be all grasped, and therefore the oil deterioration condition can be accurately detected as well. As a comparative example, the relation between the amount of n-pentane undissolved components and the mileage according to a commonly-used method "ASTM D 893B" is indicated by a broken line in FIG. 15. As is clear from this graph, the amount of the n-pentane undissolved components can not be detected before the mileage reaches a certain value, and therefore this is not the index for accurately detecting the oil deterioration condition.

Next, the operation of the sixth embodiment will now be described.

When fine undissolved components such as sludges are produced in the oil, these components adhere to the micelles, formed by imide succinate, to form fine undissolved component-deposited micelles (hereinafter referred to as "deposition micelles"), and these are arrested and removed by the fine undissolved component-arresting filter 416. Namely, the deposition micelles to be arrested and removed are formed as a result of deposition of the fine undissolved components on the micelles of imide succinate having a size of about 1.5 μm, and the deposition micelles have a size greater than the mesh of the filter. As a result, the fine undissolved components of a microscopic size, which cannot be removed by ordinary filters, can be removed.

The ECU 418 judges whether or not the flow rate is below a predetermined flow rate. Here, the predetermined flow rate is obtained by experientially finding the flow rate during the idling of the engine immediately before the fine undissolved components and the deposition micelles aggregate to become large. If the ECU 418 judges that the flow rate is below the predetermined level, it feeds an output to the alarm lamp 419 to tell the operator (driver) of this. The condition in which the flow rate is below the predetermined level coincides with the condition in which a predetermined amount of fine undissolved components are accumulated in the fine undissolved component-arresting filter 416, and if the oil is further continued to be used, the fine undissolved components and the deposition micelles aggregate to become large, so that the lubricating performance of the oil is lowered.

Advantageous effects of the sixth embodiment will be described.

(1) The n-pentane undissolved components, the viscosity and the increase of the total acid value, and the decrease of the total basic value (which are conventional deterioration indexes) can be all grasped by the amount of the fine undissolved components which is used here as the deterioration index. The amount of the fine undissolved components increases generally linearly in proportion of a time period of use of the oil. Therefore, in this embodiment, the oil deterioration condition can be accurately detected.

(2) The amount of the fine undissolved components can be easily detected by measuring the rate of flow of the oil through the fine undissolved component-arresting filter 16 by the flow rate measurement portion 17. Therefore, the apparatus can be simplified in construction.

(3) The operator exchanges the oil when the alarm lamp 19 mounted on the dashboard is lit, and thus the oil can be exchanged with fresh oil immediately before the lubricating performance of the oil is lowered. Therefore, there is no risk that a burden is imposed on the engine lubricating portions 14, thereby enhancing the durability of the engine.

Seventh Embodiment

Figure 16:
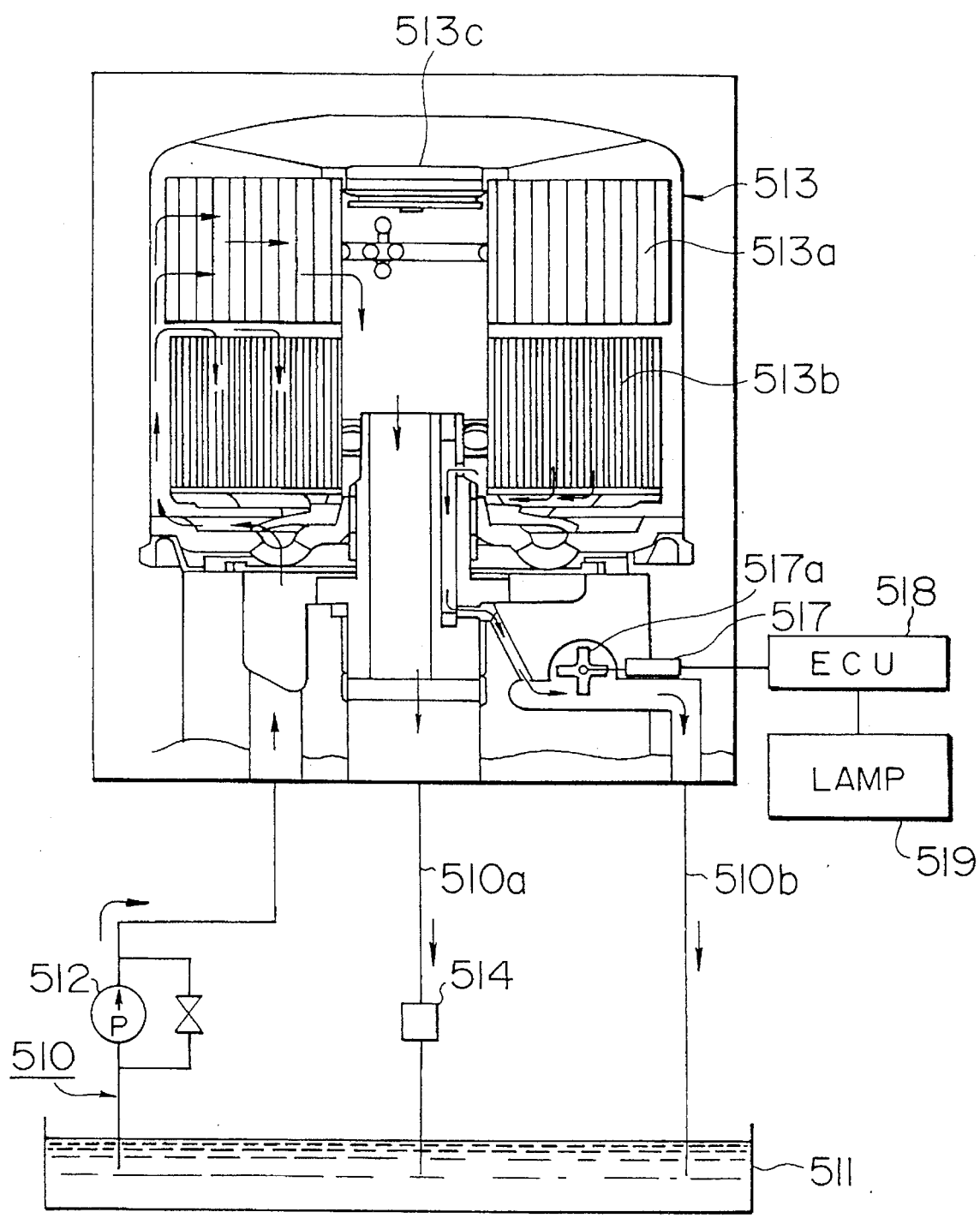
FIG. 16 is a view showing a general construction of a seventh embodiment.

Next, a seventh embodiment will now be described with reference to FIG. 16. The seventh embodiment is directed to an oil deterioration detection apparatus provided on an oil circulating line of a diesel engine.

The oil circulating line 510 is a line for feeding oil to engine lubricating portions 514. An oil pan 511, an oil pump 512, an oil filter 513 and the engine lubricating portions 514 are provided on this line. As in the sixth embodiment, imide succinate serving as a detergent-dispersant is added to the oil.

The oil pan 511, the oil pump 512 and the engine lubricating portions 514 are similar to those of the sixth embodiment, and therefore explanation thereof will be omitted.

The oil filter 513 is of the combination type in which a full-flow type and a bypass-flow type are juxtaposed. More specifically, a major part of the oil discharged from the oil pump 512 is filtered by a full-flow element 513a, and is fed to the engine lubricating portions 514 via an oil line 510a, whereas the remainder (part) of the oil is filtered by a bypass element 513b, and is returned to the oil pan 511 via an oil line 510b. As in the sixth embodiment, a relief valve 513c is mounted on the top of the oil filter 513. The full-flow element 513a used in the oil filter 513 has a relatively coarse mesh (5 µm–30 µm), and the bypass element 513b has a fine mesh (2 µm–10 µm). However, the filter mesh of the bypass element 513b is finer than that of the full-flow element 513a.

A major part of the oil from the engine lubricating portions 514 through the oil pan 511 and the oil pump 512 passes through the full-flow element 513a of the oil filter 513, so that undissolved components of a size larger than the filter mesh of this element 513a, such as wear powder, combustion products and deteriorated components resulting from the oil itself, are removed by this element 513a, thereby purifying the oil. Thereafter, the purified oil is fed through the oil line 510a to the engine lubricating portions 514. On the other hand, the remainder of the oil from the oil pan 511 and the oil pump 512 passes through the bypass element 513a, so that fine undissolved components are removed by this element, and then returned to the oil pan 511 via the bypass oil line 510b.

The oil deterioration detection apparatus of the seventh embodiment comprises the bypass element 513a serving as a fine undissolved component-arresting filter, and a flow rate measurement portion 517 serving as an oil deterioration detection means. The oil deterioration detection apparatus cooperates with an ECU 518 and an alarm lamp 519 to form an oil deterioration alarm apparatus. The flow rate measurement portion 517, the ECU 518 and the alarm lamp 519 are similar to those of the sixth embodiment, and therefore explanation thereof will be omitted. The relation between the amount of fine undissolved components, arrested by the bypass element 513b, and the running distance is generally similar to that shown in FIG. 15.

Next, the operation of the seventh embodiment will now be described.

When fine undissolved components such as carbon sludges are produced in the oil, these components form deposition micelles, and are arrested and removed by the bypass element 513b. Namely, the deposition micelles to be arrested and removed are formed as a result of deposition of the fine undissolved components on the micelles of imide succinate having a size of about 1.5 µm, and the deposition micelles have a size greater than the filter mesh. As a result, the fine undissolved components of a microscopic size can be removed.

The ECU 518 carries out a processing similar to that in the sixth embodiment, and properly judges a condition immediately before the lubricating performance of the oil is deteriorated, and causes the alarm lamp 519 to be lit, thereby telling the operator that the oil must be exchanged with fresh oil.

Advantageous effects of the seventh embodiment are generally the same as those of the sixth embodiment, and therefore explanation thereof will be omitted.

The tendency of change of the amount of the fine undissolved components used as the oil deterioration index is the same with both the gasoline engine and the diesel engine. Therefore this can be used as the deterioration index common to the gasoline engine and the diesel engine, as described in the above embodiments.

The present invention is not limited by the above embodiments, and various modifications can be made without departing from the scope of the invention.

For example, the flow rate measurement portion serving as the oil deterioration detection means may be replaced by a pressure sensor. In this case, the pressure of the oil passed the fine undissolved component-arresting filter decreases with the increase of the amount of the arrested fine undissolved components. Therefore, by detecting this pressure decrease, the amount of the fine undissolved components can be determined. In the case of the oil deterioration alarm apparatus, when the detected pressure goes below a predetermined level, the ECU feeds an output to the alarm lamp, so that the same effects as in the above embodiments can be obtained. The combination of the pressure sensor, the ECU and the alarm lamp may be replaced by a combination of a pressure switch and the alarm lamp.

As another alternative, if the temperature of the oil and an engine speed are detected and inputted to the ECU so as to compensate the flow rate detected by the flow rate measurement portion or the pressure detected by the pressure sensor, the amount of the fine undissolved components arrested by the fine undissolved component-arresting filter can be grasped more accurately. More specifically, where the output representative of the pressure is inputted to the ECU, the pressure is compensated by effecting calibration of a viscosity and etc., in accordance with the temperature of the oil, or the pressure is compensated by effecting calibration of the flow rate in accordance with the engine speed. By doing so, the amount of the fine undissolved components can be detected more accurately.

Although imide succinate is used as the detergent-dispersant in the above embodiments, the agent to be used is not limited to this material, and any other suitable material can be used in so far as it has such a nature as to uniformly disperse the fine undissolved components, such as sludges, in a stable manner.

In this case, also, the mesh of the fine undissolved component-arresting filter should be larger than the size of the micelles of the detergent-dispersant to be used, and should be smaller than the mesh of the full-flow element.

What is claimed is:

1. An apparatus for detecting a deterioration of oil, comprising:

sensor means for detecting a condition of carbon particles in the oil and for outputting a signal representative that the concentration of the carbon particles is more than a predetermined level indicative of the deterioration of the oil performance or that the particle size of the carbon particles is more than a predetermined particle size indicative of the deterioration of the oil performance, said sensor means being an optical sensor for detecting the intensity of light reflected at a detection surface of the oil with Goos-Hänchen shift, the light intensity being changed in accordance with the concentration of the carbon particles in the oil, said sensor comprising:

a light-emitting portion for emitting light toward the oil;

a photosensor for receiving the reflected light and for outputting a signal corresponding to an amount of reflected light received; and cleaning members disposed in the oil which are moved throughout the oil by the flow of the oil and are capable contacting said detection surface;

flow-out prevention members constructed and arranged to prevent said cleaning members from flowing away from a location near said detection surface while allowing the oil to flow in the vicinity of said detection surface, said cleaning members being movable within an area defined by said flow-out prevention members; and means for judging that the concentration of the carbon particles in the oil exceeds a predetermined concentration indicative of the deterioration of the oil performance when the output signal from said sensor means exceeds a predetermined value.

2. Apparatus according to claim 1, wherein said sensor comprises a prism member defining a boundary surface coincident with said detection surface, and wherein said light-emitting portion emits the light toward said boundary surface and said photosensor receives the light reflected by said boundary surface with Goos-Hänchen shift.

3. Apparatus according to claim 2, wherein said sensor includes a housing receiving said light-emitting portion, said photosensor and said prism member therein, said housing having a projected portion which is to be threaded to a container or a conduit holding the oil, and through which the oil is introduced to said boundary surface of said prism member.

4. Apparatus according to claim 1, wherein said sensor further comprises a reference photosensor for directly receiving the light emitted from said light-emitting portion.

5. Apparatus according to claim 4, further comprising:
means for compensating a change of the output signal of said photosensor, caused by a change of the amount of the light emitted from said light-emitting portion, in accordance with an output signal from said reference photosensor.

6. Apparatus for detecting particles in a liquid, comprising:
a prism member having a boundary surface in contact with the liquid to be examined;
a light-emitting portion for emitting light toward said boundary surface;
a photosensor for receiving the light reflected by said boundary surface with Goos-Hänchen shift and for outputting a signal corresponding to the amount of said received light; and
cleaning members disposed in the liquid which are moved throughout the liquid by the flow of the liquid to be examined, said cleaning members being capable of contacting said boundary surface; and
flow-out prevention members constructed and arranged to prevent said cleaning members from flowing away from a location near said boundary surface while allowing the liquid to flow in the vicinity of said boundary surface, said cleaning members being movable within an area defined by said flow-out prevention members.

7. Apparatus according to claim 6, further comprising a reference photosensor for directly receiving the light emitted from said light-emitting portion.

8. Apparatus according to claim 6, further comprising means for judging that the concentration of the particles in the liquid to be examined exceeds a predetermined concentration when the output signal from said photosensor exceeds a predetermined value.

9. Apparatus according to claim 7, further comprising:
means for judging that the concentration of the particles in the liquid to be examined exceeds a predetermined concentration when the output signal from said photosensor exceeds a predetermined value; and
means for compensating a change of the output signal of said photosensor, caused by a change of the amount of the light emitted from said light-emitting portion, in accordance with an output signal from said referenced photo sensor.

10. Apparatus according to claim 6, further comprising a housing receiving said light-emitting portion, said photosensor and said prism member therein, said housing having a projected portion which is to be threaded to a container or a conduit holding the liquid, and through which the liquid is introduced to said boundary surface of said prism member.

* * * * *